United States Patent
Da Silva Correia et al.

(10) Patent No.: US 9,012,415 B2
(45) Date of Patent: Apr. 21, 2015

(54) PHOTO-CROSSLINKED GELLAN GUM-BASED HYDROGELS: PREPARATION METHODS AND USES THEREOF

(75) Inventors: Joana Catarina Da Silva Correia, Braga (PT); Joaquim Miguel Antunes De Oliveira, Ponte GMR (PT); João Manuel Teixeira De Oliveira, Matosinhos (PT); Rui Pedro Amandi Romero De Sousa, Matosinhos (PT); Rui Luis Gonçalves Dos Reis, Oporto (PT)

(73) Assignee: Stemmatters, Biotecnologia e Medicina Regenerativa S.A., Barco (PT)

( * ) Notice: Subject to any disclaimer, the term of this patent is extended or adjusted under 35 U.S.C. 154(b) by 0 days.

(21) Appl. No.: 13/637,588

(22) PCT Filed: Mar. 26, 2011

(86) PCT No.: PCT/PT2011/000010
§ 371 (c)(1),
(2), (4) Date: Sep. 26, 2012

(87) PCT Pub. No.: WO2011/119059
PCT Pub. Date: Sep. 29, 2011

(65) Prior Publication Data
US 2013/0017177 A1 Jan. 17, 2013

(30) Foreign Application Priority Data
Mar. 26, 2010 (PT) .......................................... 105030

(51) Int. Cl.
| | | |
|---|---|---|
| *A61K 31/70* | (2006.01) | |
| *A61K 31/702* | (2006.01) | |
| *C08F 2/42* | (2006.01) | |
| *C08B 37/00* | (2006.01) | |
| *A61L 27/28* | (2006.01) | |
| *A61L 27/34* | (2006.01) | |
| *A61L 27/52* | (2006.01) | |
| *A61L 27/54* | (2006.01) | |
| *C08L 5/00* | (2006.01) | |

(52) U.S. Cl.
CPC .............. *C08B 37/006* (2013.01); *A61L 27/28* (2013.01); *A61L 27/34* (2013.01); *A61L 27/52* (2013.01); *A61L 27/54* (2013.01); *C08L 5/00* (2013.01); *A61L 2300/252* (2013.01); *A61L 2300/64* (2013.01); *A61L 2400/06* (2013.01)

(58) Field of Classification Search
USPC ............. 522/89, 178, 182, 181, 88, 168, 183, 522/162, 165, 163; 527/300, 313, 314; 526/72, 238.2, 238.3, 238.23; 514/23, 514/25, 35, 40, 54; 523/105, 111, 113, 115, 523/118
See application file for complete search history.

(56) References Cited

U.S. PATENT DOCUMENTS

| | | | |
|---|---|---|---|
| 4,631,188 A | 12/1986 | Stoy et al. | |
| 5,318,780 A | 6/1994 | Viegas et al. | |
| 5,529,914 A * | 6/1996 | Hubbell et al. | ............... 435/182 |
| 5,573,934 A | 11/1996 | Hubbell et al. | |
| 6,369,037 B1 | 4/2002 | Kim et al. | |
| 6,465,001 B1 | 10/2002 | Hubbell et al. | |
| 2002/0091229 A1 | 7/2002 | Hubbell et al. | |

FOREIGN PATENT DOCUMENTS

| | | |
|---|---|---|
| EP | 1 607 405 A1 | 12/2005 |
| WO | WO 02/18448 A2 | 3/2002 |
| WO | WO 2005/110397 A1 | 11/2005 |
| WO | WO 2006/030965 A1 | 3/2006 |
| WO | WO 2007/038982 A1 | 4/2007 |
| WO | WO 2008/002852 A2 | 1/2008 |
| WO | WO 2009/101518 A2 | 8/2009 |

OTHER PUBLICATIONS

Crescenzi, V.; et al; "New hydrogels based on carbohydrate and on carbohydrate-synthetic polymer networks" Polymer Gels and Networks, 5, 225-239, 1997.*
International Search Report and Written Opinion of the International Searching Authority, mailed Aug. 2, 2011 in connection with PCT International Application No. PCT/PT2011/000010, filed Mar. 26, 2011.
Lee, et al.; "Preparation, Characterization and Biological Properties of Gellan Gum Films With 1-ethyl-3-(3-dimethylaminopropyl)carbodiimide Cross-linker"; Carbohydrat Polymers; 2010; vol. 82, pp. 920-926.

* cited by examiner

*Primary Examiner* — Sanza McClendon
(74) *Attorney, Agent, or Firm* — Leason Ellis LLP.

(57) ABSTRACT

This invention refers to photo-crosslinked hydrogel materials based in gellan gum suitable for tissue engineering and regenerative medicine applications or as drug delivery systems. Formulations of gellan gum with different degrees of acylation serve as precursor material for insertion of a polymerizable moiety. The materials are capable of free radical polymerization with a photo-initiator at mild temperatures and exposure to ultraviolet light, enabling control of reticulation and withstanding the encapsulation of human and animal cells and/or drugs, and any combination thereof. The physicochemical and biological properties can be adjusted by combining different formulations of gellan gum and reaction conditions. The matrix can be used either as an acellular or cellular system, dispensed manually or automatically by injection and crosslinked directly at the site of application, and can be processed using manual or automated systems in different types of scaffolds, such as hydrogels, fibers, 3D structures and micro- or nanoparticles.

19 Claims, 10 Drawing Sheets

PHOTO-CROSSLINKED GELLAN GUM-BASED HYDROGELS: PREPARATION METHODS AND USES THEREOF

CROSS-REFERENCE TO RELATED APPLICATIONS

This application is a §371 national stage of PCT International Application No. PCT/PT2011/000010, filed Mar. 26, 2011, claiming priority of Portuguese Patent Application No. 105030, filed Mar. 26, 2010, the contents of each of which are hereby incorporated by reference in their entirety.

TECHNICAL FIELD

The present invention relates to photo-crosslinked gellan gum hydrogels which are capable of undergoing free radical polymerization to be used as biodegradable matrix in acellular and cellular systems for tissue engineering and regenerative medicine applications or as drug delivery systems (DDS). Methods of modifying gellan gum to make it polymerizable and for hydrogel photo-crosslinking using certain sources of light are provided. The system is biocompatible and could be dispensed manually or automatically and polymerized in situ. These new hydrogels enable a controlled reticulation process that withstands the encapsulation of cells and/or drugs, creating versatile systems that can be applied in several settings of a tissue engineering approach.

STATE OF THE ART

Hydrogels present appealing properties for tissue engineering and regenerative medicine applications, and DDS: they swell and retain large amounts of water, are tissue mimetic and can be delivered using little invasive procedures (i.e., injection). In addition, hydrogels provide a highly hydrated microenvironment (resembling ECM) and they can be injected and crosslinked in situ for allowing cell encapsulation and preservation/induction of their differentiated phenotype. An injectable hydrogel should also present a sol-gel transition mechanism suitable for clinical purposes, i.e., it should be liquid to facilitate homogeneous cell distribution and injection, while being capable of rapidly gelling after implantation. This unique combination of characteristics makes them also useful in drug delivery applications.

Although a number of hydrogel systems based in natural polymers (e.g., alginate and chitosan) have been developed to tackle, for example, cartilage regeneration, they still present several problems such as variability of production, inability to be processed at mild temperatures, poor water solubility, inadequate mechanical properties and uncontrolled degradation rates. We are proposing the use of a gellan gum-based injectable system for the aforementioned applications. This polymer is an extracellular microbial polysaccharide that forms a gel in the presence of metallic ions. Gellan gum has been studied for applications in the cartilage tissue engineering field and further experiments are ongoing to consolidate its therapeutic potential.

The chemical structure of gellan gum has been described as a linear anionic hetero-polysaccharide consisting of glucose-glucuronic acid-glucose-rhamnose as a repeating unit. This type of hydrogel presents some interesting features that allow its use as an in vivo injectable system. It is commercially available in two forms, acetylated and deacetylated both forming thermo-reversible gels with different mechanical properties in the presence of metallic ions and upon temperature decrease. It is acid and heat resistant and gel formation occurs without the need of harsh reagents. Other advantageous features include the lack of cytotoxicity, some degree of bio-adhesiveness and the existence of a free carboxylic group per repeating unit, which can be used for improvement of functionalization. Moreover, gellan gum hydrogels have already been shown to adequately support the growth and ECM deposition of human articular chondrocytes in vitro and in vivo. Gellan gum thermo-sensitive behaviour is suitable for injectable formulations since gelation can be performed in situ at a temperature close to body temperature. However, as verified for other ionic-crosslinked hydrogels, significant dissolution can occur in vivo and structural integrity may be lost over time. Work regarding gellan gum modification, by addition of free radical polymerizable groups (namely acrylate and maleate groups), has been shown to enable the formation of a 3D biodegradable hydrogel network by polymerization under mild conditions.

Photo-polymerization has been used in recent work as an alternative method for hydrogel formation with increased structural and mechanical integrity. In this technique, polymers are modified with specific functional groups (e.g., methacrylates) that may undergo free radical polymerization in the presence of a photo-initiator at mild temperatures and upon exposure to ultraviolet (UV) light. This polymerization reaction induces the formation of covalent crosslinks between functional methacrylate groups along the backbone of the polymer chains. A fluid-solid phase transformation occurs then under physiological conditions, which is ideal for the rapid entrapment of cells in situ. Other advantages include significant temporal and spatial control of the gelation process and the possibility of using a clinically approved UV light source and a biocompatible photo-initiator. Additionally, the injected cell-loaded system is able to efficiently fill the irregular defects at the site of injury, which is extremely important when considering lesions at positions difficult to access.

The photo-polymerization of (meth)acrylates has been described for dental applications. In another work, it has been described the use of a calcium alginate hydrogel combined with methacrylated dextran to produce a composite system suitable for drug delivery.

Several patents have been granted based in the use of photo-crosslinked polysaccharides hydrogels for different applications. The following examples should be taken into account by their relevance in the area of this invention:

U.S. Pat. No. 5,334,640 describes crosslinked biocompatible compositions for encapsulating biologic compounds. These compositions comprise at least one ionically crosslinked component and one covalently crosslinked component. The crosslinkable mixtures and methods for encapsulation are also provided.

U.S. Pat. No. 6,602,975 relates to photo-polymerizable biodegradable hydrogels for use as tissue adhesives and in controlled drug delivery. Hydrogels polymerized using free radical initiators under the influence of long wavelength UV light, visible light excitation or thermal energy are described.

WO 2004029137 refers to functionalized chondroitin sulphate and crosslinked polymer matrices comprising functionalized chondroitin sulphate to be used for tissue engineering, and specifically in cartilage reconstruction. Inventors describe methods of obtaining and using the functionalized polymer and the crosslinked matrices.

WO 2006036681 relates to compositions and methods for treating a tissue defect. In particular, the invention describes a hydrogel that contains at least two functional groups, one which reacts with functional groups found in cartilage or bone, and the other which is reactive with the hydrogel. A method for applying the hydrogel to the cartilage surface is provided.

US 20060057098 A1 describes a photo-reactive material which comprises a polysaccharide bound to a glycidyl ester via a covalent bond for the production of a photo-crosslinked polysaccharide by light exposure to be used in the medical field. The polysaccharide could be photo-crosslinked leading to the formation of a 3D structure that retains water, i.e., a hydrogel.

U.S. Pat. No. 7,196,180 refers to methods for functionalization of hyaluronic acid and crosslinking thereof to form hydrogels to be used as tissue adhesive or separator, drug delivery system, matrix for cell cultures and temporary scaffold for tissue regeneration. The hyaluronic acid derivatives could be crosslinked in situ by reaction with different functionalities or crosslinkers.

U.S. Pat. No. 7,365,059 describes a process for producing a photocrosslinked-polysaccharide composition which is bounded to a photo-reactive group and crosslinked by light-irradiation. The process described comprises: freezing the photo-reactive polysaccharide-containing solution, an aqueous solvent capable of dissolving the photo-reactive polysaccharide, and any one substance selected from the group consisting of alcohol having compatibility with the aqueous solvent, a surfactant and a chelating agent; and irradiating the resulting frozen product with light.

WO 2009101518 A2 refers to the application of gellan gum for regenerative medicine and tissue engineering approaches, and focus on its processing methods and devices. Concerning this application, gellan gum undergoes a controlled ionic crosslinking in the presence of a phosphate buffer, an acidic or alkaline solution.

SUMMARY

The present invention provides a photo-crosslinkable hydrogel system based in gellan gum, thereby combining the most advantageous characteristics of the biomaterial with an increased temporal and spatial control of polymerization. This system, which also allows for limited control of structural and mechanical properties of the material, is useful for tissue engineering and regenerative medicine applications, as well as for drug delivery. The present invention describes a precursor for photo cross-linking a hydrogel (also called comprising photo cross-linking precursor) a gellan gum which comprises:
at least one photo cross-linkable monomeric unit or subunit;
at least one monomeric unit or subunit chemically selective functionality for binding, preferably at least one monomeric unit or subunit chemically bounds to proteins, substances or biomolecular analites and markers.

In a preferred embodiment, the gellan gum acylation degree is from no acyl groups up to two acyl substituents—acetate and glycerate—both located on the same glucose residue, more preferably one glycerate per repeat and one acetate per every two repeats.

A more preferred embodiment the precursor further comprising a polymerizable moiety such us a methacrylates, ethacrylates, itaconates, acrylamides, aldehydes or mixtures thereof.

In another preferred embodiment the precursor above described further comprises a photo-initiator selected from free-radical initiators such as, methyl benzoylformate, 2-hydroxy-4'-(2-hydroxyethoxy)-2-methylpropiophenone or mixtures thereof.

In a more preferred embodiment the precursor above described is photo cross-linkable under aqueous conditions at any temperature between 15-37° C., in particular at room or physiological temperature.

The present invention also discloses a hydrogel material comprising precursor for photo cross-linking a hydrogel based in gellan gun above described with water or aqueous solvent. In a more preferred embodiment the precursor for photo cross-linking is between 0.01 to 2% (w/v), more preferably 1 or 2% (w/v).

In a preferred embodiment the hydrogel further comprises a photo-initiator selected from free-radical initiators. The concentrations of photo-initiator concentrations could be between 0.01 to 1% (w/v), preferably 0.1% or 0.05% (w/v).

A common photo-initiator could be methyl benzoylformate, 2-hydroxy-4'-(2-hydroxyethoxy)-2-methyipropiophenone or mixtures thereof, among others.

In a preferred embodiment, the hydrogel is able to be photo-polymerizable, namely by the use of ultraviolet rays and could also be present in the form of micro- or nanoparticles.

A more preferred embodiment of the present invention is a hydrogel material that further comprises a second non photo cross-linked gellan gum.

Another aspect of the present invention is a pharmaceutical composition comprising at least the precursor for photo cross-linking, a hydrogel object of the present invention or the hydrogel material and further comprising a biological active agent, a therapeutic agent in amounts pharmaceutically acceptable.

In a preferred embodiment the biological active agent is a cell, a stem cell, a protein, a therapeutic agent, a biomolecule, diagnostic marker and probe or a mixture thereof, encapsulated or not.

In another preferred embodiment the compositions could be present in the form of powder, aqueous solution or injectable solution.

Another aspect of the present invention is related with fibres, membranes, nets, gauzes or discs comprising the precursor for photo cross-linking or the hydrogel, object of the present invention or the hydrogel material described in the present invention, with open interconnected pores. These materials have a degree of permeability range between 0.4-4000 ($10^{-13}$ $m^4 N^{-1} s^{-1}$), preferably between 0.4-400 ($10^{-13}$ $m^4 N^{-1} s^{-1}$), more preferably between 0.4-100 ($10^{-13}$ $m^4 N^{-1} s^{-1}$).

Another embodiment of the present invention is a process for obtaining the precursor for photo cross-linking the hydrogel, one of the objects of the present invention, comprising the followings steps:
conversion of gellan gum with adequate degrees of acylation to a photo-polymerizable material through the reaction with glycidyl methacrylate. Preferably at controlled pH between 3-10, preferably 8.5 and temperature between 18-90° C.;
crosslinking of the polymer by UV light in the presence of different types of free radical initiators at mild temperatures. Preferably the radical initiator is a photo-initiator.

The precursor for photo cross-linking a hydrogel, the hydrogel, the pharmaceuticals compositions and the materials described in the present inventions could be used as biomaterial or/and in medicine.

Many different uses are possible as an injectable hydrogel solution; as coating biosensor, prosthesis and implants, a conductor transmission gel or lubricant in ultrasound equipments, in aesthetic medicine, in radio-frequency ablation medical procedures or as a nucleus pulposus implant materials.

The materials are capable of free radical polymerization with a photo-initiator at mild temperatures and exposure to ultraviolet light, enabling control of reticulation and withstanding the encapsulation of human and animal cells and/or drugs, and any combination thereof.

The physicochemical and biological properties can be adjusted by combining different formulations of gellan gum and reaction conditions.

The percursor matrix can be used either as an acellular or cellular system, dispensed manually or automatically by injection and crosslinked directly at the site of application, and can be processed using manual or automated systems in different types of scaffolds, such as hydrogels, fibres, 3D structures and micro- or nanoparticles.

BRIEF DESCRIPTION OF THE FIGURES

The following figures provide preferred embodiments for illustrating the description and should not be seen as limiting the scope of invention.

FIG. 4A shows the spectra for gellan gum and gellan gum methacrylated for 1 and 5 days of reaction. FIG. 4B illustrates the spectra for methacrylated gellan gum (1 day reaction) and photo-crosslinked discs with MBF at 1% (w/v).

FIG. 6A illustrates the DSC curves for gellan gum and methacrylated gellan gum discs equilibrated in PBS produced from methacrylated gellan gum after 1 and 5 days of reaction. FIG. 6B shows the DSC curves for methacrylated gellan gum discs equilibrated in PBS and photo-crosslinked discs with MBF at 0.1% (w/v).

FIG. 7A shows the storage (E') modulus and FIG. 7B represents the loss factor (tan δ) measured in PBS at 37° C.

DETAILED DESCRIPTION OF THE INVENTION

This invention provides photo-crosslinked gellan gum hydrogels, their processing method and use in the field of tissue engineering and regenerative medicine or DDS. With several advantages for regenerative strategies, the invented photo-crosslinkable gellan gum material provides the basis for the development of a new minimally-invasive system that could be used alone or seeded with cells suitable for restoring, maintaining or enhancing tissue(s)/organ(s) function. In addition, the polymerizable system enables the conjugation with bioactive molecules and could be used for controlled delivery of biological molecules.

Gellan gum could present different degrees of acylation: the high acyl form—presents two acyl substituents both located on the same glucose residue: on average, one glycerate per repeat and one acetate per every two repeats, produces soft, elastic, non-brittle gels; whereas the low acyl form—presents no acyl groups and produces firm, non-elastic, brittle gels. The free carboxylic groups present in the structure of gellan gum enable to confer improved functions. The insertion of a polymerizable moiety which may be selected, for example, from methacrylates, ethacrylates, itaconates, acrylamides, and aldehydes, allows obtaining a photo-reactive hydrogel.

Gellan gum with different degrees of acylation and mixtures of both isoforms were converted to a photo-polymerizable material through the reaction with glycidyl methacrylate at controlled pH (e.g., 3-10, preferably 8.5) and temperature (18-90° C.). Different degrees of methacrylation were obtained by varying the molar ratio of GMA to gellan gum repeating unit and the reaction time (e.g., from 1 hour until 15 days). The materials are biodegradable under physiological conditions due to hydrolysable bonds in the polymer backbone, resulting in non-toxic fragments that are easily removed from the body. The polymer was crosslinked by UV light in the presence of different types of photo-initiators (e.g., type I, such as benzoin ethers, benzil ketals, alfa-Dialkoxy-aceto-phenones, alfa-Hydroxy-alkyl-phenones, alfa-Amino-alkyl-phenones, Acyl-phosphine oxides; and type II such as Benzo-phenones/amines, Thio-xantones/amines) selected from free-radical initiators and at mild temperatures, such as the photo-initiator methyl benzoylformate (MBF) and 2-hydroxy-4'-(2-hydroxyethoxy)-2-methylpropiophenone (HHMPP). The insertion of methacrylate groups in gellan gum structure was verified by Fourier-transform infra-red (FTIR) analysis and proton nuclear magnetic resonance ($^1$H-NMR) spectroscopy performed before and after polymerization. The methacrylated gellan gum and photo-crosslinked hydrogels were also characterized by differential scanning calorimetry (DSC) and dynamical mechanical analysis (DMA), and its degradation and swelling properties assessed in vitro. Moreover, in vitro cytotoxicity and proliferation/viability screening was performed.

The use of different formulations, preferentially 1:1, 1:2 and 2:1 of GG-MA:photo-crosslinked GG, w:w % and reaction conditions (e.g., varying the initial GG concentration or molecular weight, varying the molar ratio of GMA to gellan gum repeating unit, reaction time and temperature, pH) allows for tailoring the final physicochemical and biological properties of the hydrogels for specific applications. One aspect of the invention is to provide an injectable scaffold or DDS with tunable physicochemical and biological properties. Formulations of the photo-crosslinkable hydrogels can use different gellan gum forms, i.e., with different degrees of acylation. These will allow obtaining scaffolds possessing a wide range of physical properties (e.g., strength, softness, flexibility, durability, degradability) according to the desired use. Along with having adjustable properties, this system also provides the advantage of being dissolved in aqueous solutions at mild temperatures and allowing spatial and temporal control of hydrogel formation, which is dependent on the application of the crosslinking agent.

These photo-crosslinked gellan gum-based hydrogels, used alone or in combination with bioactive species and/or cells, provide different possibilities for application in tissue engineering and regenerative medicine strategies. Regarding their application in this area, these materials could be deposited by manual methods or using a 3D automatic dispensing device, being crosslinked before, during or after deposition.

Fibres of photo-crosslinked gellan gum-based are prepared with different formulations of gellan gum-MA:MBF preferentially 1:0.01, 1:0.05 and 1:0.1 w:w % in water, at room temperature. Then, an appropriate volume of the mixture(s) are transferred to a device possessing a cylinder such as a 20 mL syringe. By pressing the syringe piston, it is possible to dosage the mixture through the movement along the longitudinal axis of the cylinder and through a needle of different shape and diameter, into an aqueous medium. Finally, fibres possessing the diameter of the needle used are obtained by exposing the gel to UV light. Preferred, the device may be used to transfer the mixture into a water-free or hydrophobic surface, a tri-dimensional mould with the shape of a fibre (e.g., optical fibre), which comprise the UV light itself. This system allows obtaining hollow fibres.

Preferred Synthesis of Methacrylated Gellan Gum

Figure 1:
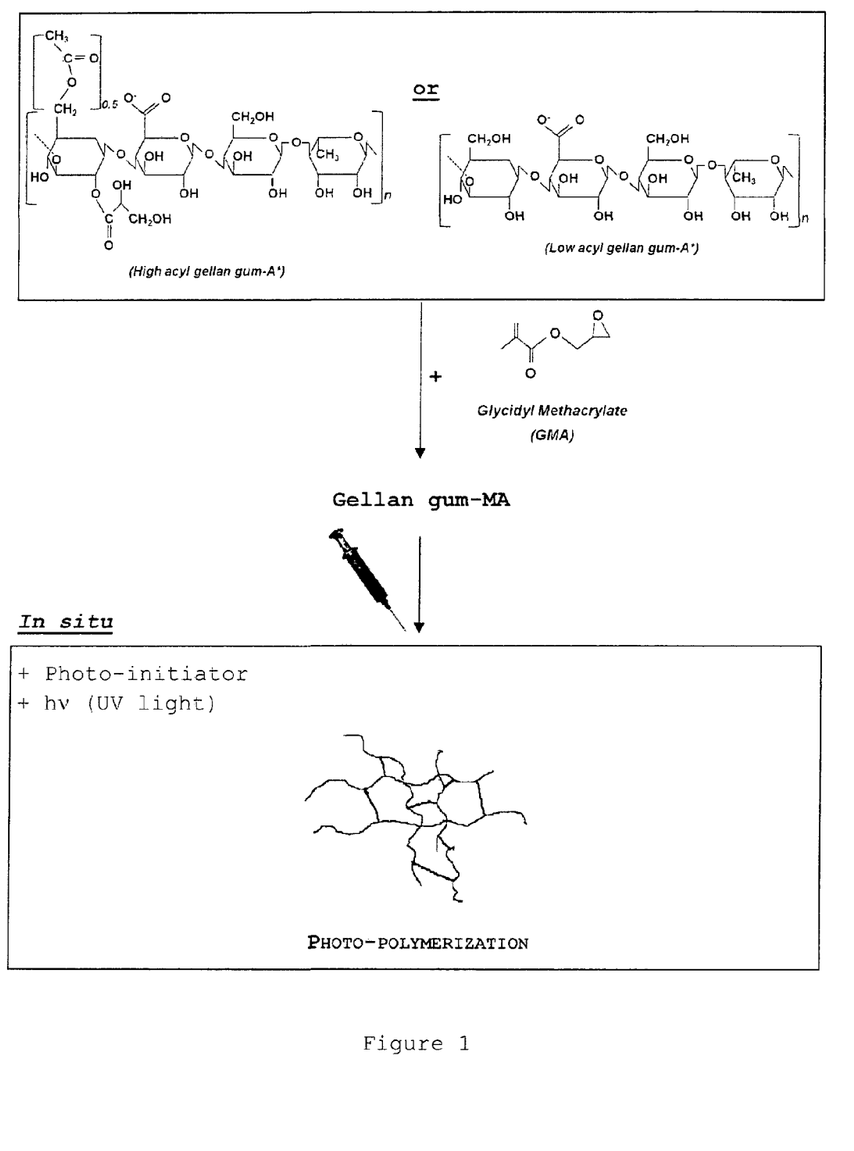
FIG. 1 represents the strategy for the development of injectable photo-crosslinkable scaffolds, which could be used with or without encapsulated cells for human tissue regeneration. The strategy is based on methacrylate modification with glycidyl methacrylate (GMA) and in situ photo-polymerization of gellan gum.
Figure 2:
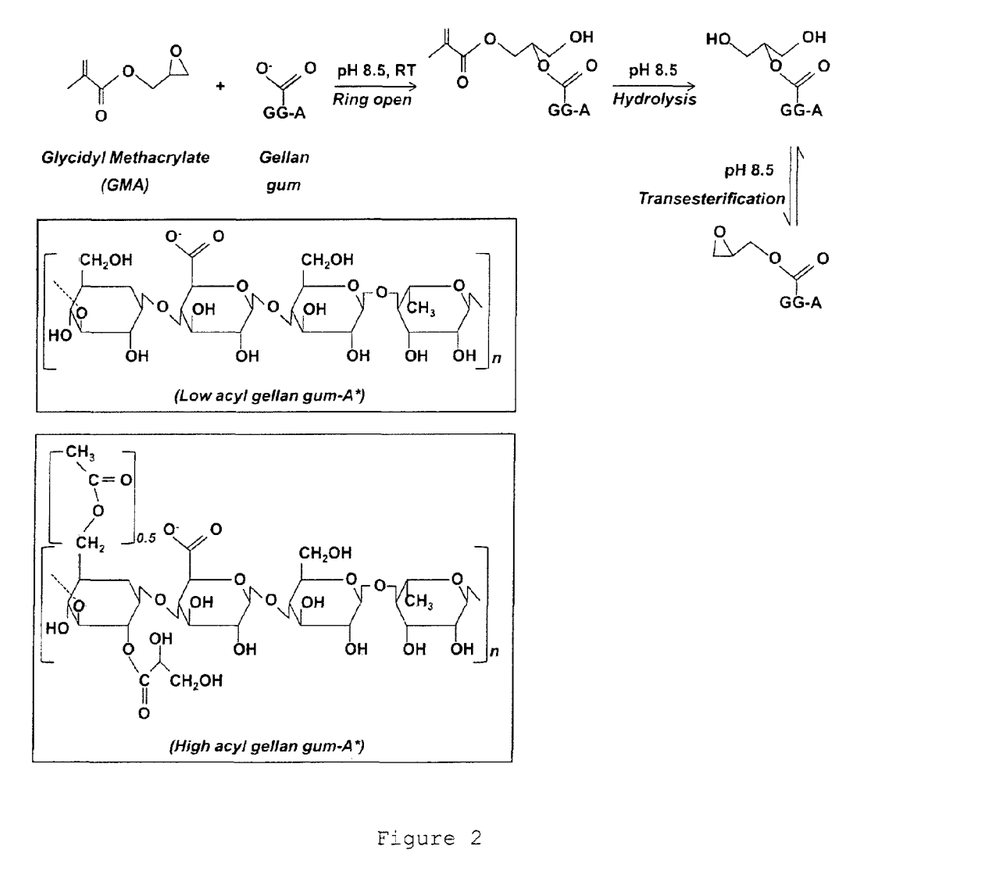
FIG. 2 represents the schematic illustration of the pH-controlled reaction (pH 8.5) of glycidyl methacrylate with gellan gum (* indicates the repeating unit of low or high acyl gellan gum consisting of glucose-glucuronic acid-glucose-rhamnose).

Preferably, the methacrylated gellan gum (gellan gum-MA) was prepared by reacting gellan gum with glycidyl methacrylate (FIG. 2). Gellan gum was dissolved in distilled water at room temperature under constant stirring to obtain a final concentration of 1% (w/v). Different compositions of commercially available gellan gum were tested: 1) low acyl gellan gum (Gelzan®, Sigma); 2) high acyl gellan gum (Kelcogel® LT 100, CP Kelco) and 3) different mixtures of both isoforms. A homogeneous dispersion of the material was achieved after heating the solution to 90° C. Alternatively, prior to methacrylation reaction, gellan gum was dialyzed against deionized water for several days. After lyophilization, the purified product was dissolved in distilled water to yield a 1% (w/v) solution. At room temperature, GMA (97%) was added to the solution at different molar ratios to the repeating unit of gellan gum. The solution was adjusted to a pH of 8.5 with 1 M NaOH and the reaction occurred with vigorous stirring at room temperature for different periods of time. The pH was automatically adjusted to 8.5 using 1 M NaOH during reaction. Different degrees of substitution were achieved either by varying the molar ratio of GMA and the reaction time. After each time point, the reaction products were precipitated with ½ volume of cold acetone and purified by dialysis against deionized water for 4 days to remove residual GMA. The purified products were frozen at −80° C. and recovered by lyophilization.

Preferred Hydrogel Formation

Figure 3:
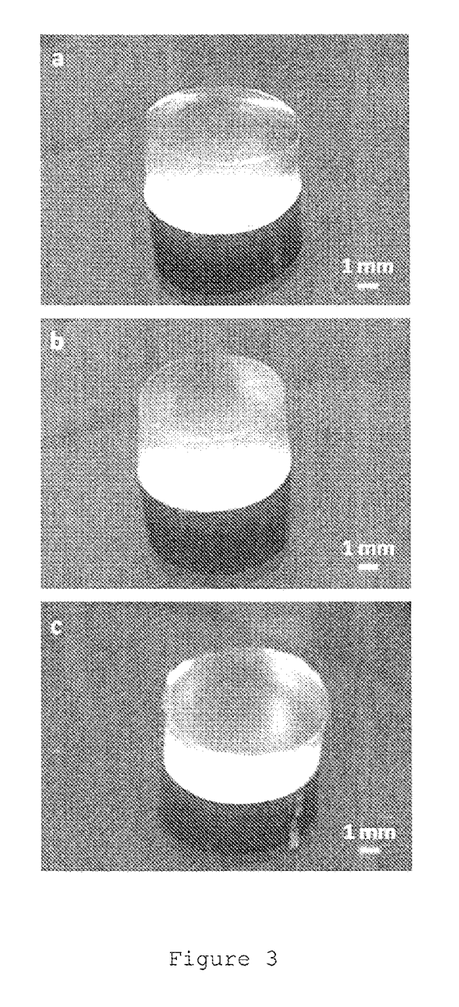
FIG. 3 illustrates the discs produced from methacrylated gellan gum (1 day of reaction) after being a) equilibrated in a phosphate buffered saline (PBS) solution, or photo-crosslinked crosslinked with: b) methyl benzoylformate (MBF) 0.1% (w/v) at 366 nm or c) 2-hydroxy-4'-(2-hydroxyethoxy)-2-methylpropiophenone (HHMPP) 0.05% (w/v) at 240-300 nm.

Preferably, to produce photo-crosslinked gellan gum hydrogels, a solution of 2% (w/v) of gellan gum-MA was prepared in deionized water. The gellan gum-MA presents an advantage over non-methacrylated gellan gum as it may be easily dissolved at body temperature (37° C.). The photo-initiator methyl benzoylformate (MBF) was added at different concentrations ranging from 0.05 to 1% (w/v). A different type of photo-initiator, 2-hydroxy-4'-(2-hydroxyethoxy)-2-methylpropiophenone (HHMPP) was also tested at concentrations between 0.05 and 1% (w/v). Gels with a cylindrical shape were prepared with a typical diameter of 6 mm (FIG. 3). Methacrylated gellan gum hydrogel discs were also obtained by immersion in a phosphate buffered saline (PBS) solution at pH 7.4. The photo-crosslinked gellan gum hydrogels were produced by exposing the gels to UV light for different time periods. The photo-crosslinked discs can be further equilibrated in PBS.

Characterization of Photo-Crosslinked Gellan Gum-Based Hydrogels

Fourier-Transform Infra Red (FTIR) Analysis

Figure 4:
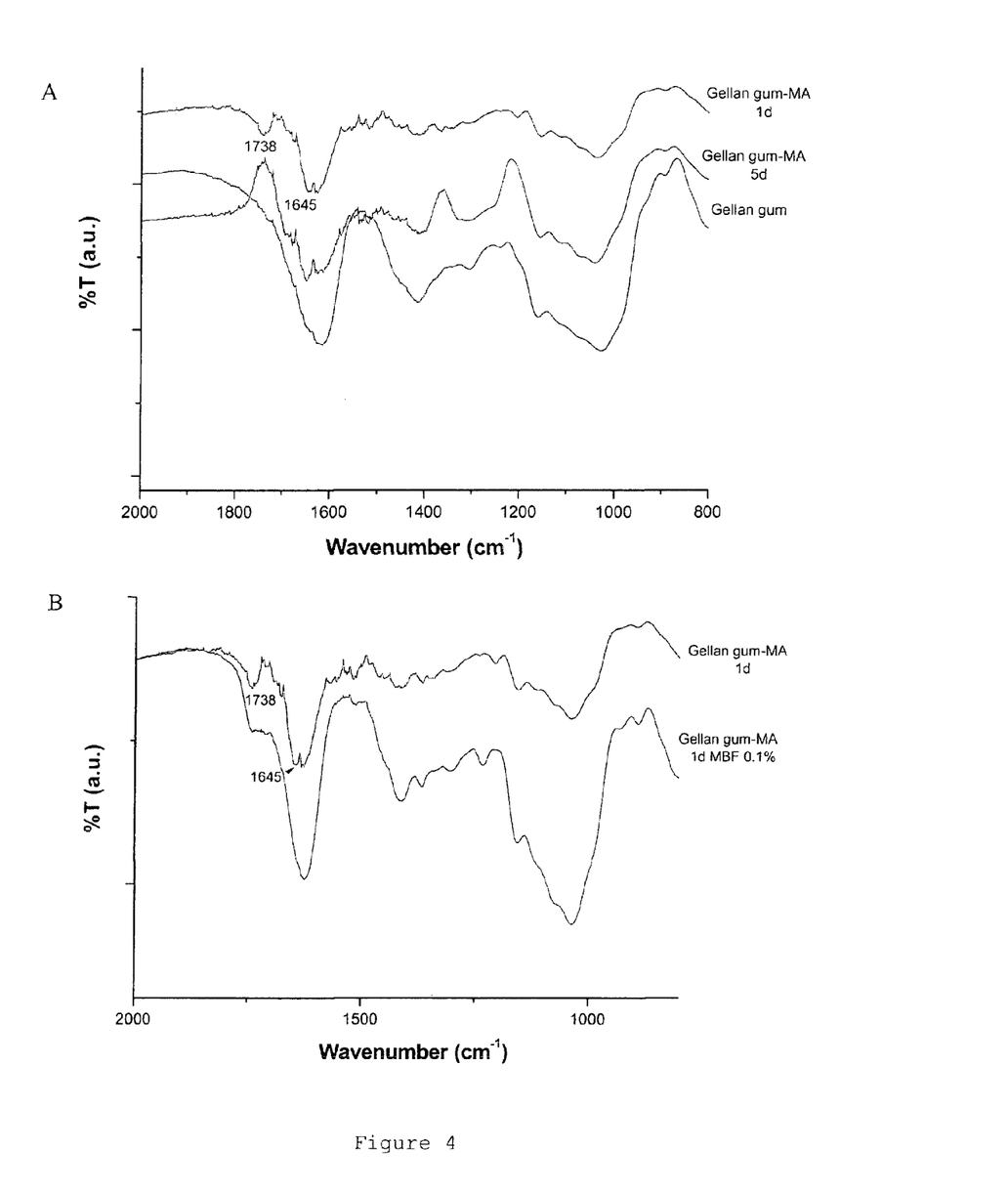
FIG. 4 represents the Fourier-transform infra-red (FTIR) of gellan gum, gellan gum-MA and photo-crosslinked gellan gum-MA.

The efficiency of methacrylation was evaluated before and after photo-crosslinking by FTIR analysis. The infrared spectra of freeze-dried samples were recorded at room temperature at a resolution of 2 $cm^{-1}$ in the range 4400-800 $cm^{-1}$ for an average of 32 scans (FIG. 4). FIG. 4A shows the FTIR spectra of gellan gum and gellan gum methacrylated for 1 and 5 days. In all spectra, typical gellan gum absorption bands were found (i.e., 1618, 1412 and 1037 $cm^{-1}$). The FTIR analysis revealed also the presence of new peaks at 1738 and 1645 $cm^{-1}$ in the methacrylated polymer, which are characteristic of carbonyl stretching vibration of an ester ($vC=O$) and double bound ($vC=C$) stretches, respectively. The appearance of new adsorption bands, which are characteristic of GMA, indicates a successful incorporation of methacrylate groups in the structure of gellan gum.

FIG. 4B illustrates the FTIR spectra of photo-crosslinked discs produced in the presence of photo-initiator MBF at 1% (w/v). The FTIR analysis revealed polymerization of methacrylate groups during UV exposure demonstrated by the inexistence of the absorption peak at 1645 $cm^{-1}$ in the photo-crosslinked discs. Moreover, it was observed a decrease in the absorption band at 1738 $cm^{-1}$ identified in gellan gum methacrylated for 1 day. The reduction of this band, assigned to carbonyl stretching vibration of an ester ($vC=O$) from GMA, can be indicative of successful polymerization.

The results from FTIR analysis demonstrated that methacrylated gellan gum was successfully produced and that this material is able to undergo photo-polymerization in the presence of the photo-initiator MBF.

$^1$H-NMR Spectroscopy

Figure 5:
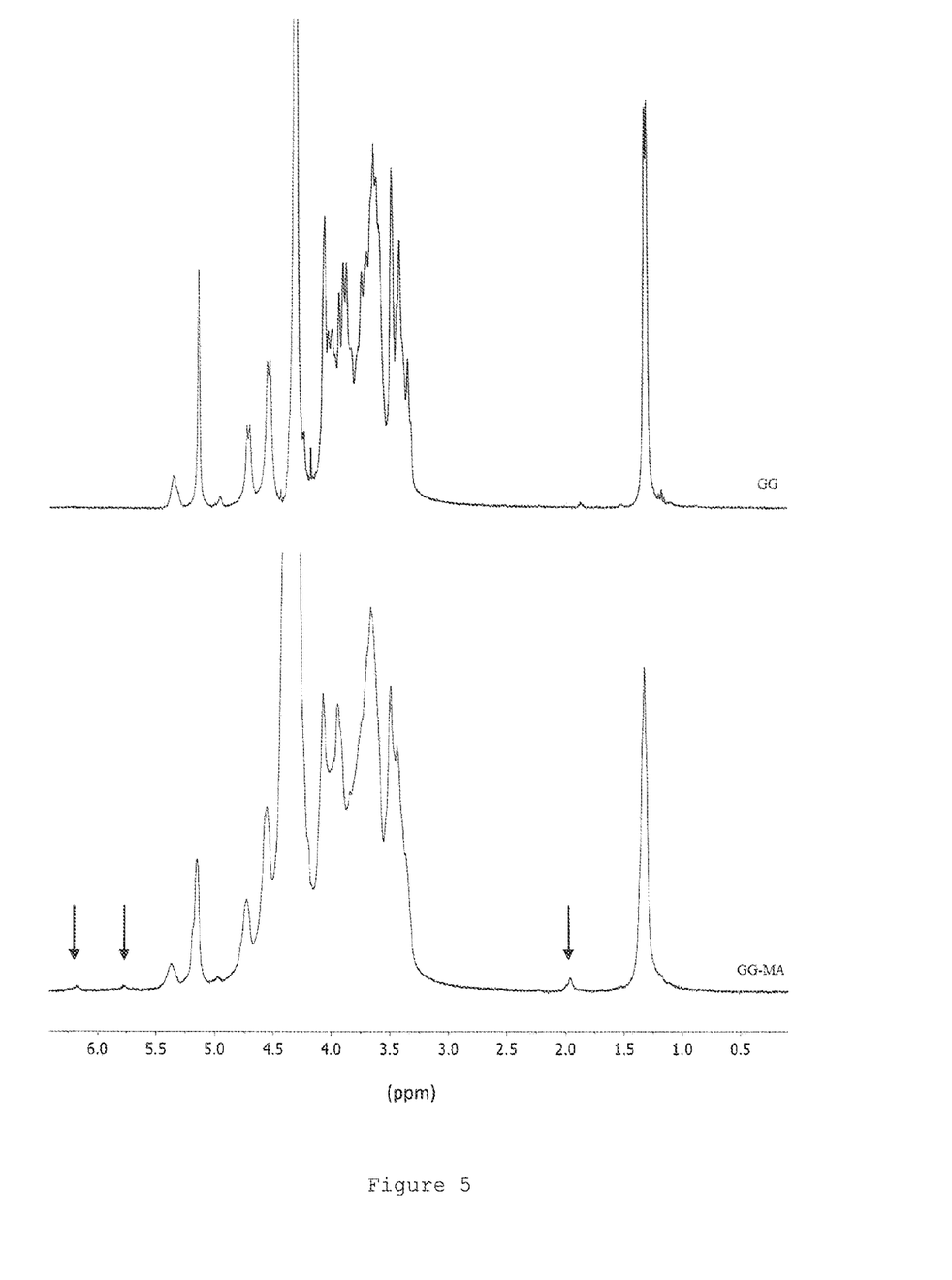
FIG. 5 represents the proton nuclear magnetic resonance ($^1$H-NMR) spectra of gellan gum (GG) and methacrylated gellan gum (GG-MA) performed in $D_2O$ at 70° C. The arrows indicate the peaks corresponding to the protons newly formed from the reaction of GG with GMA.

The insertion of methacrylate groups in gellan gum structure was corroborated by $^1$H-NMR analysis. FIG. 5 shows the $^1$H-NMR spectra of gellan gum and gellan gum-MA powders dissolved in deuterium-d2 water ($D_2O$) recorded at 70° C. The $D_2O$ peak at 4.3 ppm was used as reference.

The chemical shift for unmodified gellan gum presented characteristic signals at 5.15 and 1.32 ppm, corresponding to H-1 and H-6 of the α-anomers of L-rhamnopyranosyl residue. Additionally, the signals at 4.73 ppm and 4.55 ppm should be attributed to D-glucopyranosyl and D-glucuropyranosyl residues, respectively. These characteristic signals were also present in the chemical shift for gellan gum-MA.

The gellan gum-MA spectra also showed the appearance of singlets at 1.96 (due to the methyl proton of methacrylate), 5.77 and 6.18 ppm (both from the vinyl-proton), which are ascribed to the protons newly formed from the reaction of gellan gum with GMA.

These data clearly revealed that methacrylation was successfully achieved.

DSC Analysis

Methacrylated gellan gum hydrogels (equilibrated in PBS) and photo-crosslinked discs were produced at 2% (w/v) concentration from gellan gum methacrylated for 1 and 5 days according to the procedure described in preferred hydrogel formation. Gellan gum discs were also prepared at 2% (w/v) concentration as described elsewhere by Oliveira et al. (J Biomed Mater Res A 2009), and were used as controls.

Figure 6:
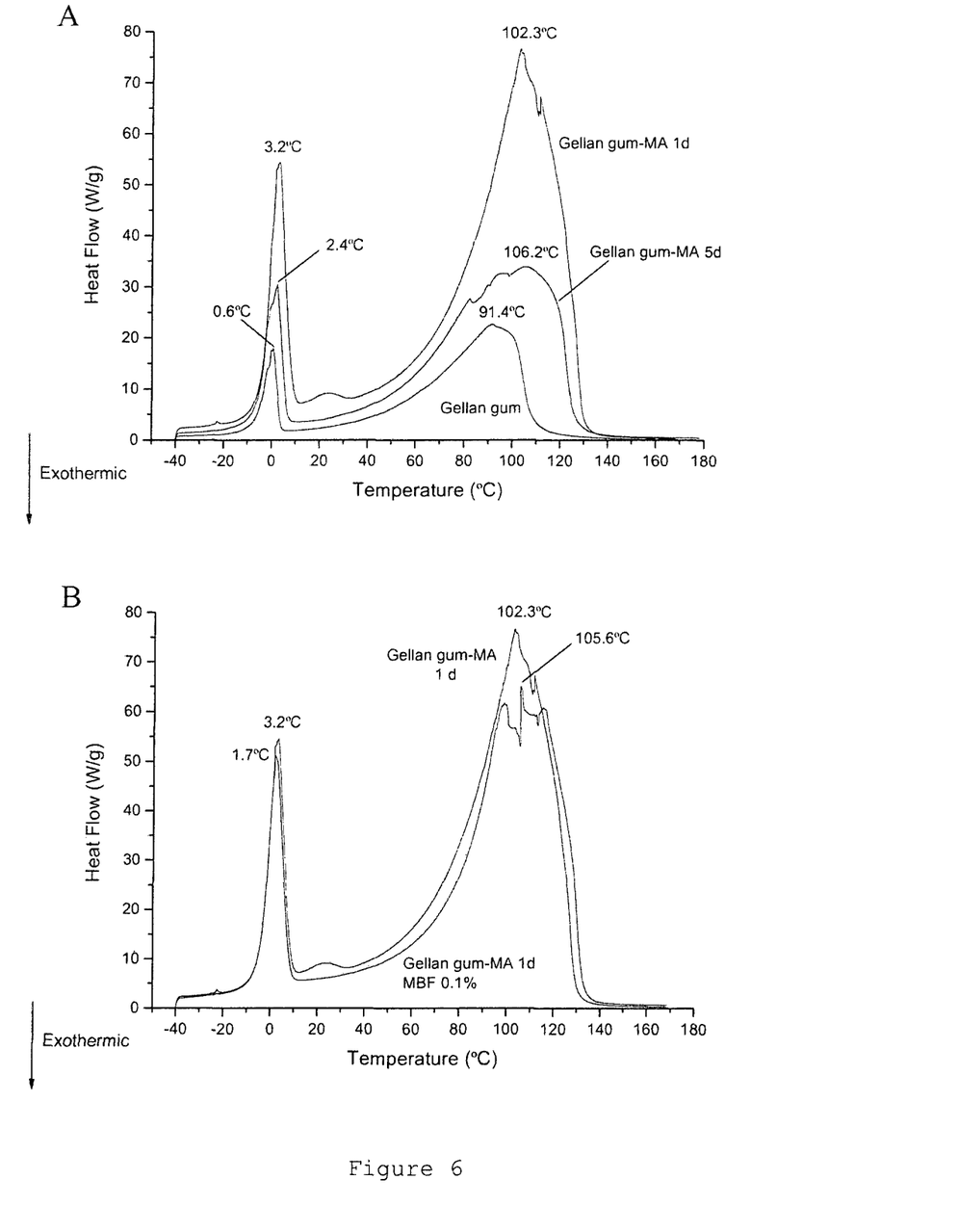
FIG. 6 represents the heating differential scanning calorimetry (DSC) curves of gellan gum, gellan gum-MA immersed in PBS and photo-crosslinked gellan gum-MA discs.

FIG. 6A displays the DSC profiles of gellan gum and gellan gum methacrylated for 1 and 5 days. The appearance of two or more endothermic peaks in the heating DSC curves of methacrylated gellan gum may be an indication of the presence of junction zones with different bonding energies or different rotational freedoms. Higher temperature endothermic peaks, as observed for gellan gum-MA, could be attributed to the melting of the zones with higher bonding energies or with lower rotational freedoms.

FIG. 6B shows the DSC profile of photo-crosslinked discs produced in the presence of photo-initiator MBF at 0.1% (w/v) using gellan gum methacrylated for 1 day. Once more, the appearance of multiple endothermic peaks in the heating DSC curves of photo-crosslinked gellan gum suggests the existence of connections with different thermal stabilities.

The DSC results reveal that methacrylated gellan gum and photo-crosslinked gellan gum-MA form ordered structures involving more thermally stable junction zones.

Dynamic Mechanical Analysis (DMA)

The mechanical behaviour of the modified gellan gum hydrogel discs was characterized by DMA. Methacrylated gellan gum hydrogels and photo-crosslinked discs were produced at 2% (w/v) concentration from gellan gum methacrylated for 1 day, according to preferred hydrogel formation. Gellan gum discs were also prepared at 2% (w/v) concentration as described by Oliveira et al. (J Biomed Mater Res A 2009), and were used as controls. Discs with 7 mm diameter and 4 mm height were produced by using a cylindrical silicone mould.

Figure 7:
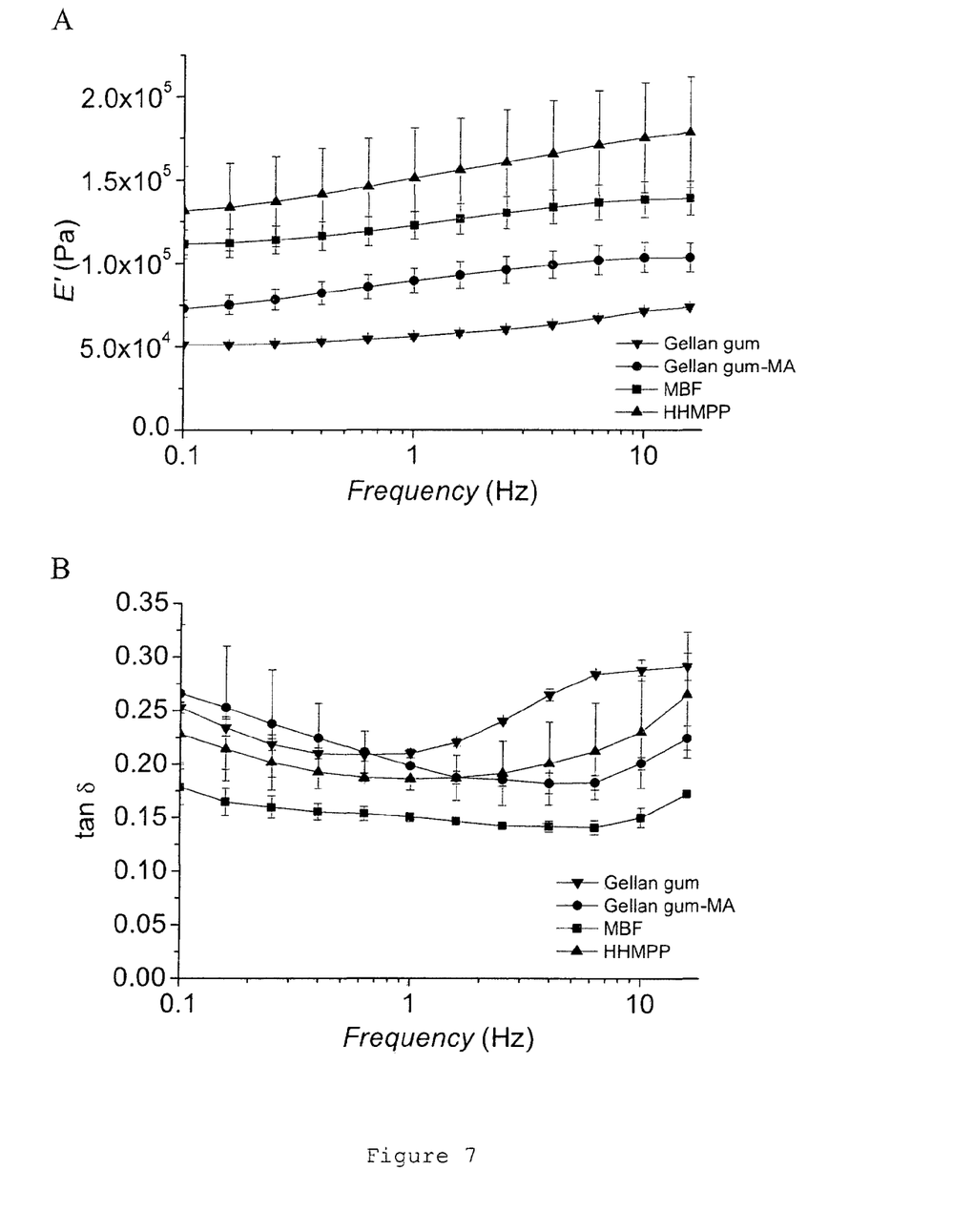
FIG. 7 represents the dynamical mechanical analysis (DMA) of the developed hydrogel discs (i.e., gellan gum, gellan gum-MA equilibrated in PBS and photo-crosslinked gellan gum-MA discs with MBF 0.1% (w/v) and 0.05% (w/v) HHMPP).

FIG. 7 shows the DMA of gellan gum-based hydrogel discs measured in wet state (PBS) at 37° C., throughout a physiological relevant frequency range (0.1-15 Hz). The mechanical behaviour of gellan gum discs was compared to methacrylated gellan gum and photo-crosslinked gellan gum-MA discs with either 0.1% (w/v) MBF or 0.05% (w/v) HHMPP. The storage modulus of the hydrogels increased by means of increasing frequency, but it presented a viscoelastic-like behaviour (FIG. 7A). This means that the tested hydrogels are elastic in a certain extent. The storage modulus at 1 Hz of photo-crosslinked gellan gum-MA discs with MBF (122.8±8.3 kPa) and HHMPP (151.2±29.9 kPa) is higher as compared to that for gellan gum hydrogels (56.2±1.4 kPa). This can be attributed to the more compact microstructure, i.e., higher crosslinking density. The higher crosslinking degree, the higher elasticity will present the hydrogels discs. Methacrylated gellan gum-MA hydrogels presented an intermediate behaviour (89.5±7.4 kPa).

Loss factor (tan δ) for gellan gum, methacrylated gellan gum and photo-crosslinked gellan gum-MA discs is shown in FIG. 7B. Values varied between 0.15 and 0.21 at 1 Hz, with gellan gum displaying the higher value. Differences in water retention and microstructure compaction of the hydrogels may explain these observations.

DMA results revealed that photo-crosslinked hydrogels display improved mechanical properties. This data shows that mechanical performance can be tailored by adjusting the reaction and processing conditions.

In Vitro Degradation and Swelling Capacity

Discs at 2% (w/v) made of gellan gum-MA equilibrated in PBS or photo-crosslinked with 0.1% (w/v) MBF or 0.05% (w/v) HHMPP were prepared according to the procedure described in preferred hydrogel formation, and lyophilized afterwards. Gellan gum discs were also prepared at 2% (w/v) concentration as described by Oliveira et al. (J Biomed Mater Res A 2009), and were used as controls.

Figure 8:
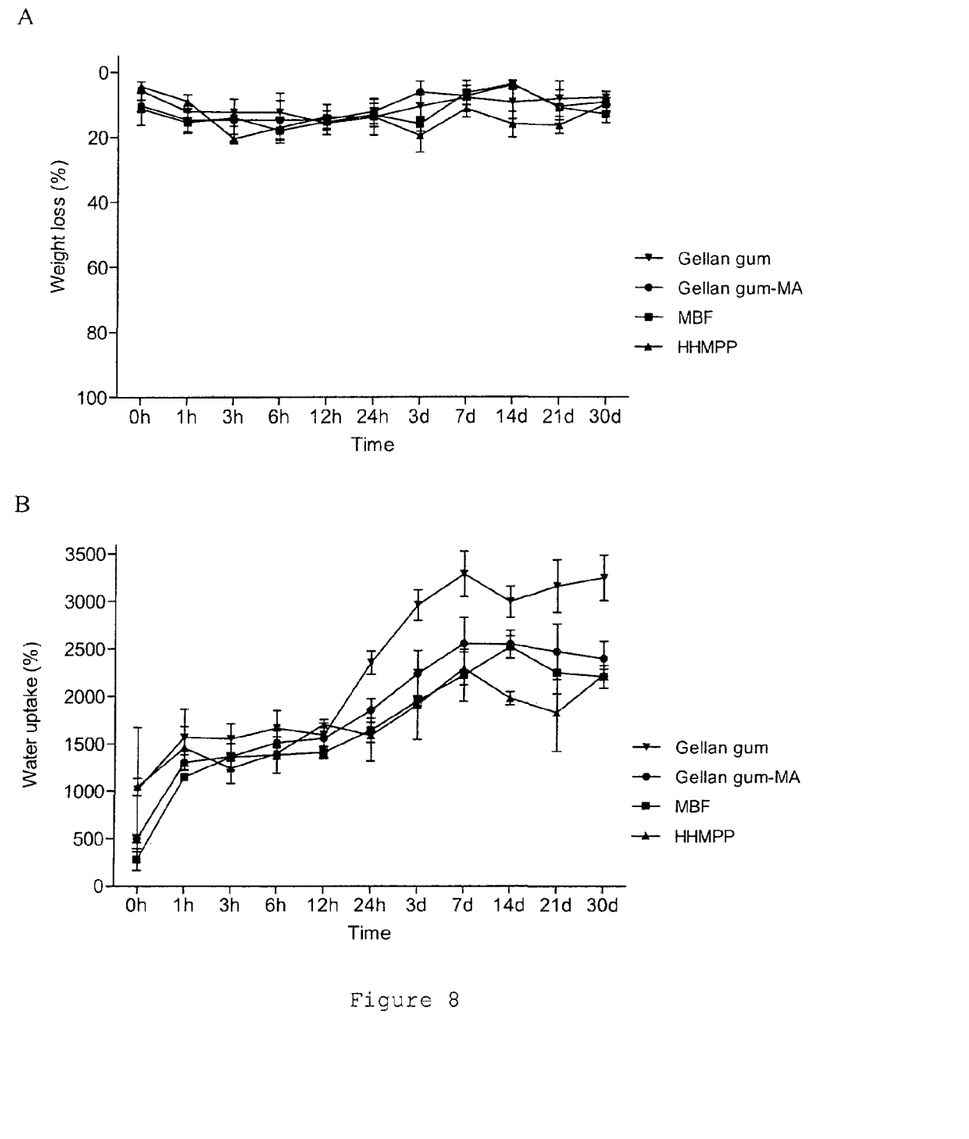
FIG. 8 represents the weight loss (A) and water uptake (B) of gellan gum discs, gellan gum-MA discs equilibrated in PBS and photo-crosslinked discs with MBF 0.1% (w/v) and 0.05% (w/v) HHMPP.

FIG. 8 shows the weight loss and water uptake ability of the developed hydrogels soaked in PBS (pH 7.4) at 37° C. under constant agitation (60 rpm), for different time periods. Weight loss results showed that no significant degradation was observed for all the freeze-dried hydrogel discs tested (i.e., gellan gum, methacrylated gellan gum and photo-crosslinked gellan gum-MA with MBF and HHMPP), after 30 days (FIG. 8A). Despite, different weight loss profiles can be seen among the materials.

Regarding the swelling ability of the hydrogels, the values for water uptake in all the hydrogel discs obtained from gellan gum-MA (i.e., methacrylated gellan gum-MA and photo-crosslinked gellan gum-MA with MBF and HHMPP) were lower as compared to those for gellan gum (FIG. 8B). This can be attributed to a higher crosslinking density, consistent with a tighter matrix, which thus is less able to swell.

These results indicate that methacrylated gellan gum enables to form a more structurally stable matrix, particularly by photo-polymerization.

Assessment of the Cytotoxicity of Photo-Crosslinked Gellan Gum-Based Hydrogels

The cytotoxicity of the photo-crosslinked hydrogels prepared from methacrylated gellan gum after 1 day of reaction was assessed using an immortalized mouse lung fibroblasts cell line (L929) purchased from European Collection of Cell Cultures (ECACC, UK). L929 cells were grown as monolayer's in Dulbecco's modified Eagle's medium (DMEM) supplemented with 10% (v/v) foetal bovine serum and 1% (v/v) of an antibiotic-antimycotic mixture containing 10,000 U·mL$^{-1}$ penicillin G sodium, 10,000 μg·mL$^{-1}$ streptomycin sulphate and 25 μg·mL$^{-1}$ amphotericin B as Fungizone® Antimycotic in 0.85% saline. The L929 cells were incubated at 37° C. in a humidified atmosphere with 5% $CO_2$, and the medium changed every two days. The investigation of the potential effect of leachables released from the materials (within a 24 hours extraction period) on cellular metabolism was performed using a standard MTS (3-(4,5-dimethylthiazol-2-yl)-5(3-carboxymethoxyphenyl)-2(4-sulfofenyl)-2H-tetrazolium) viability test in accordance with ISO/EN 10993 part 5 guidelines. This assay is based on the bioreduction of the substrate MTS into a brown formazan product by dehydrogenase enzymes in metabolically active cells, being widely used for evaluation of cell viability. Discs at 2% (w/v) made of gellan gum-MA equilibrated in PBS or photo-crosslinked with 0.1% (w/v) MBF or 0.05% (w/v) HHMPP were prepared as previously described under sterile conditions in 48-well plates by adding a volume of 125 μL per well. Gellan gum discs with similar dimensions were also processed at 2% (w/v) as described by Oliveira et al. (J Biomed Mater Res A 2009), and used as controls. The materials were previously sterilized by ethylene oxide. The extracts fluids were prepared according to the literature. Briefly, a minimum of 41 discs with a diameter of 15 mm were introduced in 50 mL tubes containing 20 mL of complete DMEM culture medium to produce the extracts. The tubes were incubated in a thermostatic bath at 37° C. and 60 rpm for 24 hours. Confluent L929 cells were detached from the culture flasks using trypsin (0.25% trypsin/EDTA solution) and a diluted cell suspension was prepared. Cells were then seeded in each well of a 96-well plate (six replicates per sample) at a density of $2 \times 10^4$ cells per well. Afterwards, cells were incubated for 24 hours at 37° C. in an atmosphere with 5% $CO_2$ for achieving 80-90% of confluence. The culture medium in each well was removed and replaced by an identical volume (200 μL) of the extraction fluids. After 1, 3 and 7 days, the extracts were removed and 300 μL of a mixture containing serum-free culture medium without phenol red and MTS (CellTiter 96 One solution Cell Proliferation Assay kit) was added to each well. After incubation for 3 hours at 37° C. and with 5% $CO_2$, the optical density (OD) was measured at 490 nm using a plate reader. A latex rubber extract was used as positive control for cell death and culture medium was used as a negative control representing the ideal situation for cell proliferation. The percentage of cell viability was calculated after normalization with the mean OD value obtained for the negative control. All tests were performed in triplicate. Statistical analysis was performed with GraphPad Prism using one-way analysis of variance followed by Bonferroni post-test and significance set at $p<0.05$ for n=18.

Figure 9:
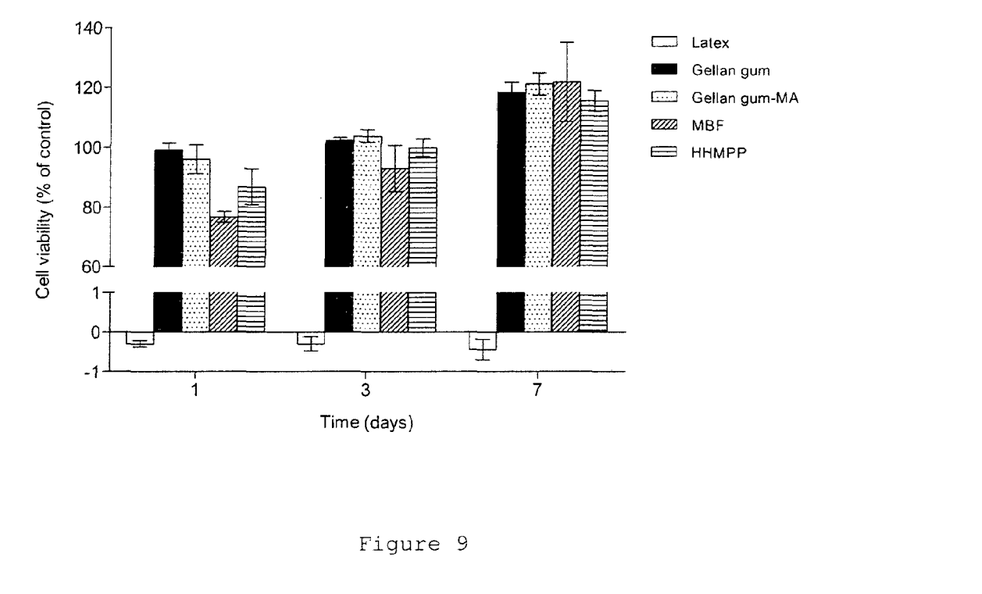
FIG. 9 graphically represents the cytotoxic evaluation of the leachables released from the discs produced from gellan gum, methacrylated gellan gum equilibrated in PBS and photo-crosslinked methacrylated gellan gum.

The results obtained with MTS cytotoxicity test showed that L929 cells were metabolically active after contacting with the different extract fluids for all the periods tested (FIG. 9). No statistically significant differences were found between the materials and negative control, and all the materials were considered to display a non-cytotoxic behavior. From the results, it can be concluded that the degree of methacrylation and the concentration of the photo-initiator (MBF or HHMPP) do not have a deleterious effect on cellular metabolism. It was also clearly observed a toxic effect of the positive control for cell death (latex) on cell viability (FIG. 9).

Biological Performance of Photo-Crosslinked Gellan Gum-Based Hydrogels

The ability of photo-crosslinked gellan gum-MA hydrogels to sustain cells viability was assessed using nucleus pulposus (NP) cells isolated from New Zealand white rabbit intervertebral discs (IVDs). The New Zealand white rabbit is an outbred breed of the albino rabbit, middle sized animal often used for animal experiments, particularly for IVD regeneration studies. Rabbit NP cells were isolated using an enzymatic-based method (collagenase type II). Briefly, after animal sacrifice, the extracted discs were placed in PBS solution (pH 7.4) and washed several times with PBS containing 1% (v/v) antibiotic-antimycotic mixture until total removal of blood or other bodily contaminants. NP tissue was then separated from any obvious dense annulus tissue and after being washed several times with PBS containing 1% (v/v) antibiotic-antimycotic mixture, NP tissue digestion was performed by incubation at 37° C. in a humidified atmosphere of 5% $CO_2$ for 24 hours in 10 mL of cell medium DMEM:F12 (1:1) supplemented with 10% (v/v) FBS, 1% (v/v) of an antibiotic-antimycotic mixture and 0.01% (v/v) collagenase II. A cell strainer (100 μm) was used to separate the cells from the remaining tissue debris. The isolated NP cells were expanded in DMEM:F12 (1:1) medium supplemented with 10% (v/v) FBS and 1% (v/v) of an antibiotic-antimycotic mixture until reaching confluence. After two cell passages, cells were detached from the culture flasks using trypsin (0.25% trypsin/EDTA solution) and a diluted cell suspension was prepared and centrifuged at 1200 rpm for 5 minutes. For the encapsulation in the photo-crosslinked hydrogel, the medium was completely aspirated and the cell pellet was re-suspended in gellan gum-MA hydrogel (methacrylated for 1 day) containing 0.1% (w/v) MBF. The mixture of cells and hydrogel was centrifuged at 600 rpm for 3 minutes to allow homogenization of cells. The mixture was then used to produce discs with a typical diameter of 7 mm using a silicone mould (200 μl per disc). The discs with encapsulated NP cells were then exposed to UV light to allow photo-polymerization. Afterwards, the discs were incubated for different time periods in DMEM:F12 (1:1) medium.

Cell viability after specific times of culturing (3 and 14 days) was assessed using Calcein AM staining. Briefly, a Calcein AM solution of 1/1000 was prepared in culture medium. Photo-crosslinked discs with encapsulated rabbit NP cells were collected from the culturing plates and incubated in the Calcein AM solution for 15-30 min at 37° C. and afterwards washed in sterile PBS. The samples were then observed under a fluorescence microscope.

Figure 10:
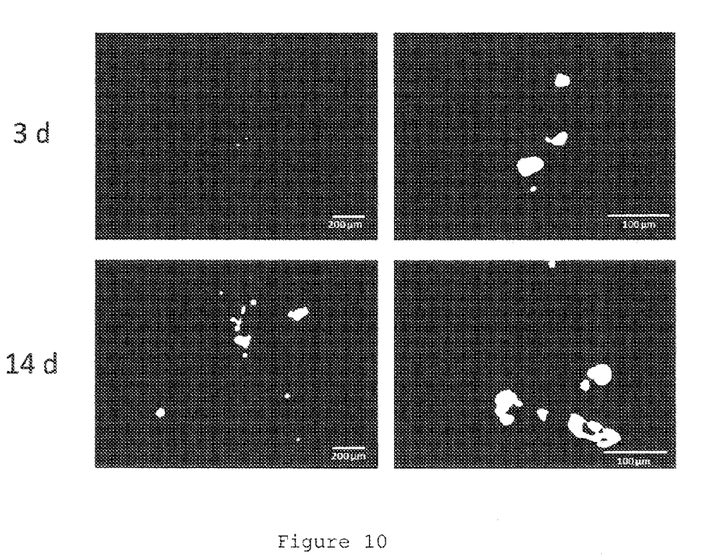
FIG. 10 illustrates cell viability of nucleus pulposus (NP) cells isolated from rabbit intervertebral discs (IVDs) and encapsulated in photo-crosslinked discs with 0.1% (w/v) MBF, after 3 and 14 days of culturing (cells were stained with Calcein AM and observed under fluorescence microscopy).

Calcein AM staining showed a uniform distribution of viable NP cells in the photo-crosslinked discs, after 3 and 14 days of culturing (FIG. 10). From images, it is possible to observe cells spreading which is an indication of cells activation. An increasing density of live cells was observed which demonstrate that these hydrogels supports cells proliferation.

The invention is of course not in any way restricted to the embodiments described and a person with ordinary skill in the art will foresee many possibilities to modifications thereof without departing from the basic idea of the invention as defined in the appended claims.

The following claims set out particular embodiments of the invention.

The invention claimed is:

1. A precursor for photo cross-linking a hydrogel comprising a gellan gum comprising:
   (a) at least one photo-reactive monomeric unit or subunit;
   (b) at least one monomeric unit or subunit having a chemical functional group for binding wherein this functional group is a carboxylic group,
   wherein the gellan gum acylation degree is one glycerate per repeating unit and one acetate per every two repeating units, wherein the repeating unit is a glucose-glucuronic acid-glucose-rhamnose tetrasaccharide.

2. The precursor according to claim 1, wherein the said functional group is able to bind to proteins, biomolecular analytes or markers.

3. The precursor according to claim 1 further comprising a polymerizable moiety such as a methacrylate, an ethacrylate, an itaconate, an acrylamide, an aldehyde or any mixture of any of the preceding.

4. The precursor according to claim 1 further comprising a photo-initiator, in particular a free-radical photo-initiator.

5. The precursor according to claim 4, wherein the photo-initiator is methyl benzoylformate, 2-hydroxy-4'-(2-hydroxyethoxy)-2-methylpropiophenone or mixtures thereof.

6. A coating for a prosthesis, a biosensor or an implant comprising the precursor according to claim 1.

7. A hydrogel material comprising the precursor according to claim 1 and water or an aqueous solvent.

8. The hydrogel material according to claim 7, wherein the concentration of precursor is 0.01 to 4% (w/v).

9. The hydrogel material according to claim 7, wherein the range of photo-initiator concentration is between 0.01 to 1% (w/v).

10. The hydrogel material according to claim 7 in the form of micro- or nanoparticles.

11. The hydrogel material according to claim 7, further comprising a second, non-photo-cross-linked gellan gum.

12. A pharmaceutical composition comprising the precursor according to claim 1 and a biologically active or therapeutic agent selected from the group consisting of a cell, a stem cell, a protein, a therapeutic agent, a biomolecule, diagnostic marker, and a probe or any mixture of any of the preceding.

13. A composition according to claim 12 in the form of a powder, an aqueous solution or an injectable solution.

14. A fibre, membrane, net, gauze or disc comprising the precursor according to claim 1.

15. A fibre, membrane, net, gauze or disc comprising the hydrogel material according to claim 7, having a degree of permeability in the range between 0.4-4000 ($10^{-13}$ $m^4$ $N^{-1}s^{-1}$).

16. A process for obtaining the precursor of claim 1 comprising the following steps:
    (a) reacting the gellan gum with glycidyl methacrylate at a pH of between 3-10 to convert the gellan gum to a photo-polymerizable material; and
    (b) crosslinking the photo-polymerizable material of step a) with UV light in the presence of a photo-initiator to obtain the precursor at a temperature between 18-37° C.

17. The process according to claim 16, wherein step a) is performed at a pH 8.5 and at a temperature between 18-37° C.

18. The process according to claim 16, wherein the photo-initiator of step b) is a free radical initiator.

19. The precursor according to claim 1 comprising at least one photo-reactive monomeric unit or subunit comprising methacrylate as a polymerizable moiety.

* * * * *